United States Patent [19]

Suzuki et al.

[11] Patent Number: 5,253,983
[45] Date of Patent: Oct. 19, 1993

[54] AXIAL PISTON PUMP HAVING FIXED SLANT CAM PLATE FOR CAUSING RECIPROCATION OF PISTONS

[75] Inventors: Shigeru Suzuki; Kunifumi Goto; Wataru Minami, all of Kariya, Japan

[73] Assignee: Kabushiki Kaisha Toyoda Jidoshokki Seisakusho, Kariya, Japan

[21] Appl. No.: 734,891

[22] Filed: Jul. 24, 1991

[30] Foreign Application Priority Data

Aug. 1, 1990 [JP] Japan .............................. 2-81980[U]

[51] Int. Cl.$^5$ ............................................. F04B 39/02
[52] U.S. Cl. .................................... 417/485; 417/499; 91/6.5
[58] Field of Search ................... 417/485, 499; 91/6.5

[56] References Cited

U.S. PATENT DOCUMENTS 2,944,529  7/1960  Wiggermann ........................ 91/6.5
3,905,274  9/1975  Week ..................................... 91/6.5

Primary Examiner—Richard A. Bertsch
Assistant Examiner—Roland G. McAndrews, Jr.
Attorney, Agent, or Firm—Brooks Haidt Haffner & Delahunty

[57] ABSTRACT

An axial piston pump, for pumping an operating oil in a hydraulic system, comprises a rotary cylinder block having a plurality of cylinder bores formed therein and disposed at regular intervals around a rotational axis thereof. Each bore is opened at a bottom thereof through a hole formed in an end wall of the cylinder block, a plurality of pistons being slidably received in the bores, respectively. Further, the pump comprises a fixed slant cam plate engaged with the pistons during a rotation of the block, for causing a reciprocation of the pistons within the cylinder bores, and a fixed valve plate having a suction port and a discharge port. The block end wall is resiliently pressed against the valve plate so that the holes of the bores are operatively connected with the suction and discharge ports of the valve plate during the rotation of the block. The valve plate has an annular seal land formed thereon and surrounding the ports, to thereby form an annular oil groove around the annular seal land, and a plurality of bearing lands formed at regularly spaced intervals along a periphery of the valve plate member, to thus form a radial oil passage between two adjacent bearing lands. The radial oil passage is at least partially defined by a cylindrical surface or sloped surface so that a penetration of the operating oil from the radial oil passage into a fine space between the bearing lands and the cylinder block end wall.

8 Claims, 5 Drawing Sheets

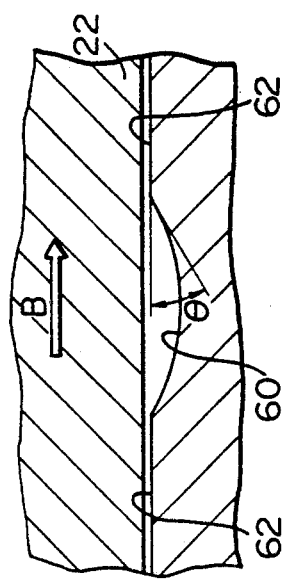
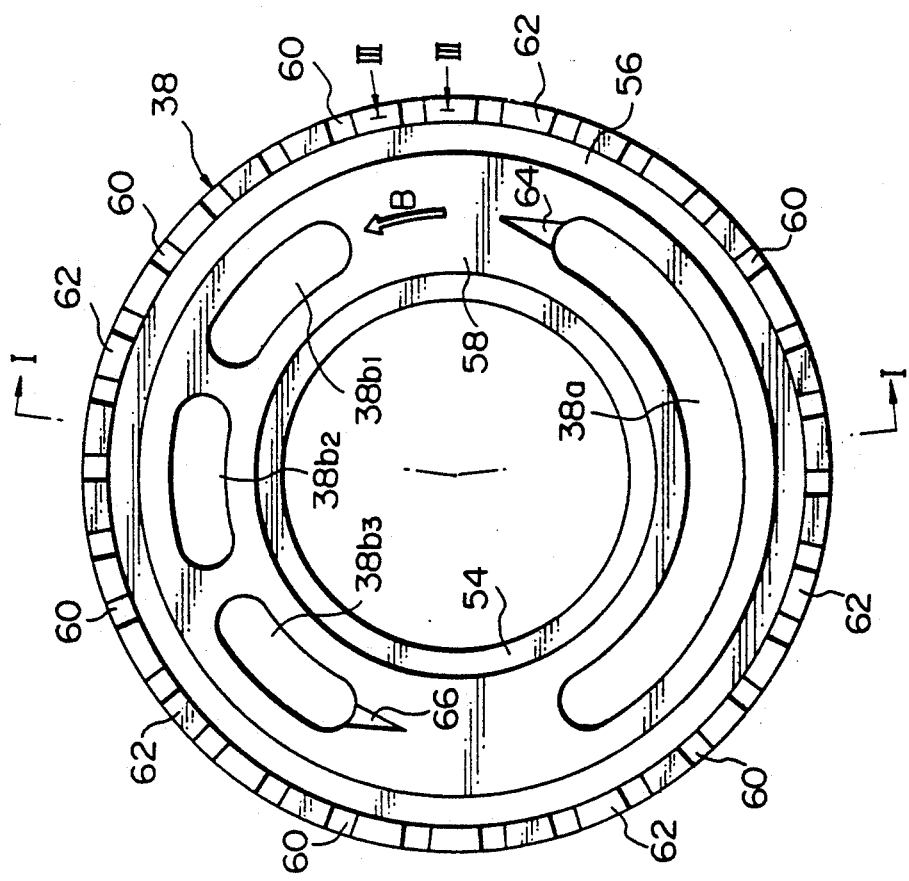

AXIAL PISTON PUMP HAVING FIXED SLANT CAM PLATE FOR CAUSING RECIPROCATION OF PISTONS

BACKGROUND OF THE INVENTION

1) Field of the Invention

The present invention relates to an axial piston pump for pumping an Operating oil through a hydraulic system, and more particularly, it relates to such an axial piston pump having a fixed slant cam plate for causing a reciprocation of the pistons therein.

2) Description of the Related Art

In an axial piston pump of this type, the pistons are slidably received in cylinder bores formed in and around a rotational axis of a rotary cylinder block, at regular intervals, respectively. Each of the pistons has a spherical end portion projecting from the cylinder bore, and this spherical end is slidably received and held in a spherical recess formed in a shoe element. The shoe element is slidably engaged with the fixed slant cam plate, and is supported by a rotatable retaining member that maintains the slidable engagement between the fixed slant cam plate and the shoe element. This arrangement enables the pistons to be reciprocated in the bores of the cylinder block, respectively, during a rotation of the cylinder block.

Each of the cylinder bores of the rotary cylinder block is opened at the bottom thereof through a hole formed in an end wall of the cylinder block, and these holes are disposed at regular intervals along a circle having a center thereof located on the rotational axis of the cylinder block. The cylinder block is disposed in such a manner that the end wall thereof faces a fixed annular valve plate having an arcuate suction port and an arcuate discharge port, and is resiliently pressed against the valve plate so that the suction and discharge ports thereof are laid along the same circle as that around which the holes of the cylinder block are disposed. Further, the arcuate suction and discharge ports of the valve plate are positioned in such a manner that, when each of the holes of the cylinder block passes through the arcuate suction port during the rotation of the cylinder block, the piston associated with that hole is in a suction stroke, and when each of the holes of the cylinder block passes through the arcuate discharge port during the rotation of the cylinder block, the piston associated with that hole is in a discharge stroke. Therefore, when the pump is incorporated into a hydraulic system, it operates in such a way that the operating oil is sucked up through the arcuate suction port of the valve plate into the cylinder bores and is discharged from the cylinder bores through the arcuate discharge port thereof.

During the pumping operation of the pump as mentioned above, a leakage of the operating oil occurs at the contact wall surfaces between the valve plate and the cylinder block end wall, to form a lubricating oil film therebetween, but this leakage must be kept as small as possible, to ensure an efficient operation of the pump. To this end, conventionally, the valve plate has an annular seal land formed thereon and surrounding the arcuate suction and discharge ports, and the cylinder block end wall is brought into a sealing engagement with the annular seal land of the valve plate. In this arrangement, a peripheral annular groove is formed between the cylinder block end wall and the valve plate, and serves as a guide passage for the leaked operating oil. In this conventional pump, further, the cylinder block is susceptible to a vibrational play during the rotation thereof, because no support of the peripheral annular portion of the cylinder block end wall can be provided due to the presence of the peripheral annular groove of the valve plate, and accordingly when the vibrational play occurs at the rotating cylinder block, the leakage of the operating oil becomes larger and the efficiency of the pump is thus lowered.

To prevent the vibrational play of the cylinder block, it has been suggested in Unexamined Japanese Patent publication No. 47(1972)-44201 (Kokai) that a plurality of segment-shaped bearing lands be located at regularly spaced intervals along the periphery of the valve plate, to support the peripheral annular portion of the cylinder block end wall. Namely, the vibrational play of the cylinder block can be effectively prevented because the peripheral annular portion of the cylinder block end wall can be supported by the segment-shaped bearing lands, during the rotation of the cylinder block. Note, with this arrangement an annular oil passage is formed between the annular seal land and the segment-shaped bearing lands, and a plurality of radial oil passages are formed between the adjacent segment-shaped bearing lands.

Nevertheless, in this pump, the annular seal land of the valve plate suffers greater wear than the segment-shaped bearing lands thereof. In particular, since the operating oil inevitably includes very small pieces of grit such as metal powders, and these very small pieces of grit are contained in the oil films formed between the wall end of the cylinder block and the annular seal land and segment-shaped bearing lands, these small pieces of grit in the oil films act as an abrasive on the contact surfaces between the cylinder block end wall and the seal and bearing lands. The oil film formed between the cylinder block end wall and the annular seal land has a higher pressure than that of the oil films formed between the cylinder block end wall and the segment-shaped bearing lands, because these segment-shaped bearing lands are separated from the annular seal land by the annular oil passage intervened therebetween, and because they are arranged at regularly spaced intervals along the periphery of the valve plate to form the plurality of radial oil passages between the adjacent segment-shaped bearing lands. Accordingly, the contact surfaces between the cylinder block end wall and the annular seal land of the valve plate suffer more wear than the contact surfaces between the cylinder block end wall and the segment-shaped bearing lands thereof, and thus an undesirable clearance can be formed between the cylinder block end wall and the annular seal land of the valve plate during a long operation of the pump, which will inevitably lower the operating efficiency of the pump.

SUMMARY OF THE INVENTION

Therefore, an object of the present invention is to provide an axial piston pump, of the type mentioned above, which is constituted such that the contact surfaces between the cylinder block end wall and the annular seal land and segment-shaped bearing lands of the valve plate are uniformly worn during a service life of the pump, to thereby prevent a formation of an undesirable clearance between the cylinder block end wall and the annular seal land of the valve plate.

In accordance with the present invention, there is provided an axial piston pump for pumping a operating oil through a hydraulic system, and comprises: a rotary cylinder block having a plurality of cylinder bores formed therein and disposed at regular intervals around a rotational axis thereof, each of the cylinder bores being opened at a bottom thereof through a hole formed in an end wall of the cylinder block; a plurality of pistons slidably received in the cylinder bores, respectively; a fixed slant cam plate member engaged with the pistons during a rotation of the rotary cylinder block, for causing a reciprocation of the pistons within the cylinder bores thereof; and a fixed valve plate member having a suction port and a discharge port, the end wall of the cylinder block being resiliently pressed against the valve plate member so that the holes of the cylinder bores are operatively connected with the suction and discharge ports of the valve plate member during the rotation of the cylinder block, whereby the operating oil is sucked up into each of the cylinder bores through he suction port of the valve plate member and the hole of that cylinder bore, and is then discharged from each of the cylinder bores through the hole of that cylinder bore and the discharge port of the valve plate member. Further, the valve plate member is provided with an annular seal land formed thereon and surrounding the suction and discharge ports, to thus form an annular groove around the annular seal land, and a plurality of bearing lands arranged at regularly spaced intervals along a periphery of the valve plate member, to thereby form a radial groove between each two adjacent bearing lands; the annular groove and radial groove being communicated with each other and serving as a guide passage for an operating oil leaked from a space between the annular seal land and the end wall of the cylinder block, and the radial oil passage being defined by a cylindrical surface or a V-shaped cross-sectional surface extended between two side edges thereof, whereby a penetration of the operating oil into a fine space between the bearing lands and the end wall of the cylinder block is facilitated.

In the present invention, the radial groove may be at least partially defined by a cylindrical surface or a sloped surface which is extended from one side edge of the radial groove, which is defined as a trailing side edge with respect to a rotating surface of the end wall of the rotary cylinder block, to a bottom of the radial groove.

BRIEF DESCRIPTION OF THE DRAWINGS

The other objects and advantages of the present invention will be better understood from the following description, with reference to the accompanying drawings, in which:

FIG. 2 is an enlarged elevation view showing the valve plate member of FIG. 1, as viewed along a line II—II of FIG. 1;

FIG. 3 is a sectional view taken along a line III—III of FIG. 2;

DESCRIPTION OF THE PREFERRED EMBODIMENTS

Figure 1:
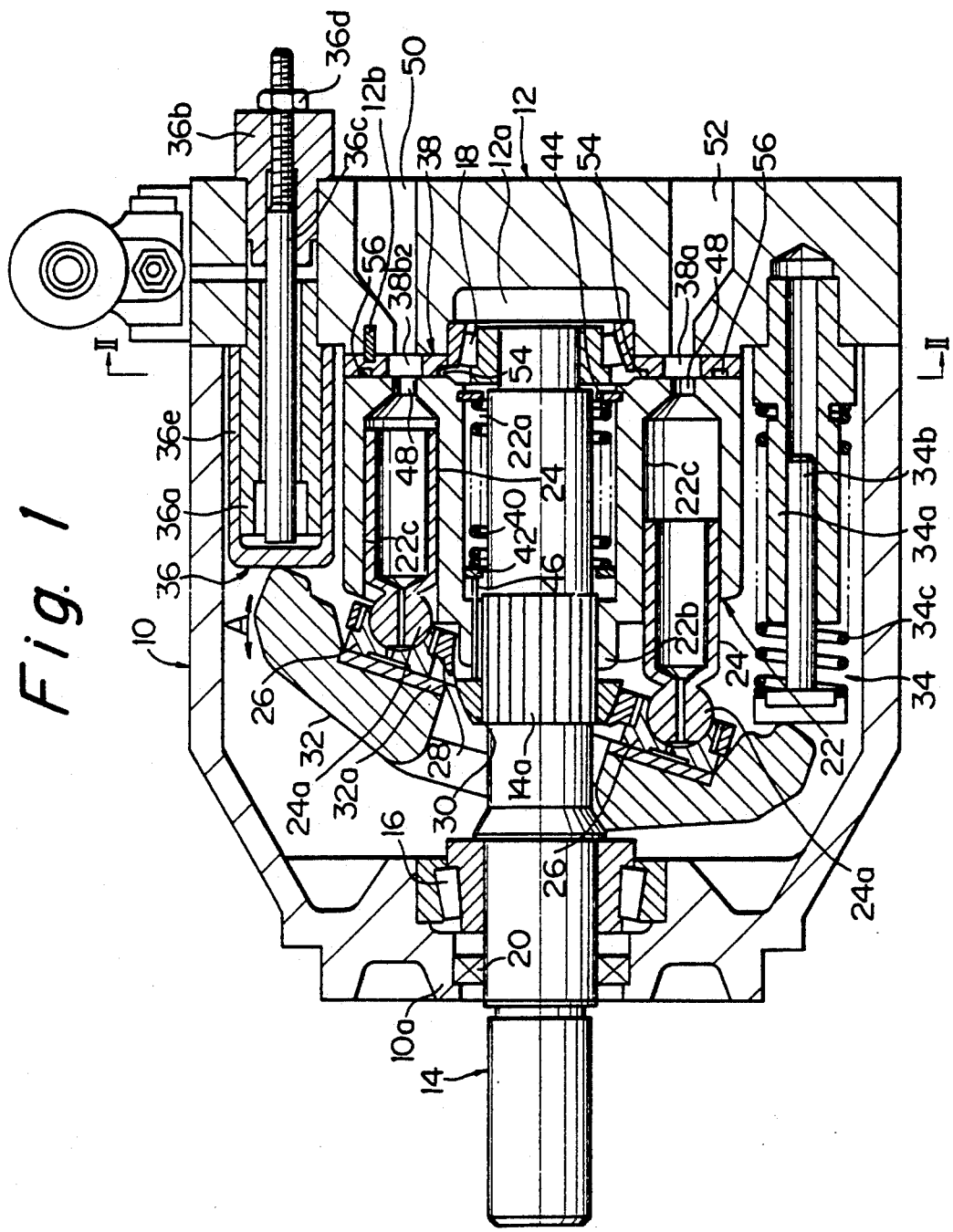
FIG. 1 is a longitudinal sectional view showing an axial piston pump according to the present invention, a valve plate member thereof being illustrated as taken along a line I—I of FIG. 2.

FIG. 1 shows a representative axial piston pump in which the present invention is embodied, which comprises a cup-like casing 10 and an end cover member 12 securely mounted to an open end face of the casing 10. A drive shaft 14 extends within the casing 10 so that a rotational axis thereof matches a longitudinal axis of the casing 10, and one end of the drive shaft 14 is projected outside from an opening formed in a neck portion 10a of the casing 10 and is operatively connected to a suitable prime mover (not shown). The drive shaft 14 is rotatably supported by a first radial bearing 16 provided in the opening of the casing neck portion 10a and by a second radial bearing 18 provided in an inner central recess 12a. A seal member 20 is provided in the opening of the casing neck portion 10a to seal an interior of the casing from the outside.

The pump also comprises a rotary cylinder block 22 having a central passage 22a through which the drive shaft 14 is extended. The cylinder block 22 has a neck portion 22b which is engaged with a spline 14a formed on the drive shaft 14, whereby the cylinder block 22 is rotated together with the drive shaft 14 and is axially slidable thereon. The cylinder block 22 has a plurality of cylinder bores 22c formed therein and disposed around a rotational axis thereof at regular intervals. The pistons 24 are slidably received in the cylinder bores 22c, respectively, and each of the pistons 24 has a spherical end 24a projecting from the corresponding cylinder bore 22c, which spherical end 24a is slidably received and held in a spherical recess formed in a shoe element 26. The shoe element 26 is rotatably supported by a retaining member 28 slidably mounted on a convex spherical surface of a mount member 30 immovably fixed to the shaft spline 14a. Namely, the retaining member 28 has a central opening defined by a concave spherical surface, and the mount member 30 is slidably received in the central opening of the retainer member 28.

The pump further comprises a fixed slant cam plate member 32 provided within the casing 10 and having a central opening through which the drive shaft 14 is extended. The fixed slant cam plate member 32 has an annular plate element 32a secured thereto and having a smooth annular cam face with which the shoe elements 26 are slidably engaged. Thus, when the drive shaft 14 is rotationally driven to rotate the cylinder block 22, the retaining member 26 is rotated together with the cylinder block 22 so that each of the pistons 24 is reciprocated in the corresponding cylinder bore 22c.

During the operation of the pump, the fixed slant cam plate member 32 is fixed or set at a given angular position, but this angular position thereof is adjustable. To this end, the slant cam plate member 32 is provided with stub shafts (not shown) projected from the sides thereof and rotatably supported by the inner side walls of the casing 10, so that the fixed slant cam plate member 32 is angularly movable in two directions as indicated by an arrow A. The adjustment of the angular position of the fixed slant cam plate member 32 is carried out by both a resilient biasing means 34 and an adjustable abutment means 36.

In particular, the resilient biasing means 34 includes a hollow guide member 34a projected from the inner wall of the cover member 12; a rod member 34b slidably received in the hollow guide member 34a and having a head portion abutted against a lower end of the slant cam plate member 32; and a compressed coil spring 34c restrained between the head portion of the rod member 34b and a shoulder formed on an outer periphery of the hollow guide member 34a. The adjustable abutment means 36 includes a first hollow guide member 36a projected from the inner wall of the cover member 12; a second hollow guide member 36b projected from the outer wall of the cover member 12; a rod member 36c slidably received in the first and second hollow guide members 36a and 36b and having a threaded end portion extended through the second hollow guide member 36b; a nut threadedly engaged with the threaded end portion of the rod member 36c; and a cup member 36e slidably passed onto the first hollow guide member 36a and abutted against an upper end of the slant cam plate member 32. Therefore, by turning the nut 36d with a suitable tool (not shown), the slant cam plate member 32 can be angularly moved in one of the directions indicated by the arrow A, to enable the slant cam plate member 32 to be fixed or set at a given angular position, whereby a stroke of the pistons 24 can be adjusted.

Futhermore, the pump comprises an annular valve plate member 38 disposed between the inner wall of the cover member 12 and an end wall of the cylinder block 22 and fixed to the former by several key elements 12b (only one illustrated). The end wall of the cylinder block 22 is resiliently pressed against the valve plate member 38 by a compressed coil spring 40 provided within the central passage 22a of the cylinder block 22. In particular, the coil spring 40 is received in the central passage 22a in such a manner that it surrounds the drive shaft 14, and is held between movable and immovable annular elements 42 and 44 received in the central passage 22a and surrounding the drive shaft 14. The movable annular element 42 is constricted by push rod elements 46 (only one illustrated) axially extending through a wall of the neck portion 22b: one end of each push rod element 46 is abutted against the movable annular element 42; and the other end thereof is abutted against the mount member 30. The immovable annular element 44 is fixed to the cylinder block 22. This arrangement allows the cylinder block 22 to be resiliently pressed against the valve plate member 38.

Each of the cylinder bores 22c of the cylinder block 22 is opened at the bottom thereof through a hole 48 formed in the end wall of the cylinder block 22, and these holes 48 are disposed at regular intervals along a circle having a center located on the rotational axis of the cylinder block 22. Further, as best shown in FIG. 2, the annular valve plate member 38 has an arcuate suction port 38a and three arcuate discharge ports $38b_1$, $38b_2$, and $38b_3$ which are disposed along the same circle as the holes 48 of the cylinder block 22. The arcuate suction port 38a is positioned such that, when each of the holes 48 passes through the arcuate suction port 38a during the rotation of the cylinder block 22, the piston associated with that hole is in a suction stroke, and the arcuate discharge ports $38b_1$, $38b_2$, and $38b_3$ are positioned such that, when each of the holes 48 passes through these arcuate discharge ports $38b_1$, $38b_2$, and $38b_3$ during the rotation of the cylinder block 22, the piston associated with that hole is in a discharge stroke. The arcuate suction port 38a is in communication with a suction passage 50 formed in the cover member 12, and the arcuate discharge ports $38b_1$, $38b_2$, and $38b_3$ are in communication with a discharge passage 52 formed in the cover member 12. Therefore, when the pump is incorporated into a hydraulic system and driven to rotate the cylinder block 22 in a direction indicated by an arrow B (FIG. 2), the operating oil is sucked up through the suction passage 50 and the arcuate suction port 38a into the cylinder bores 22c, and is then discharged from the cylinder bores 22c through the arcuate discharge ports $38b_1$, $38b_2$, and $38b_3$ and the discharge passage 52. Note, a single arcuate discharge port may be formed in place of the three arcuate discharge ports $38b_1$, $38b_2$, and $38b_3$.

The valve plate member 38 is formed with an inner annular recess 54 and an outer annular groove 56 such that an annular seal land 58 surrounds the arcuate suction port 38a and the arcuate discharge ports $38b_1$, $38b_2$, and $38b_3$, and the wall end of the cylinder block 22 is brought into sealing engagement with the annular seal land 58. Also, the valve plate member 38 has a plurality of radial grooves 60 formed along the periphery thereof such that a plurality of segment-shaped bearing lands 62 along the periphery of the valve plate member 38 support a peripheral annular portion of the end wall of the cylinder block 22. During the operation of the pump, a leakage of the operating oil occurs at the contact faces between the wall end of the cylinder block 22 and the annular seal land 58 and segments-shaped bearing lands 62, so that lubricating oil films are formed therebetween. The annular groove 56 and the radial grooves 60 are in communication with each other, and serve as an oil passage for the thus-leaked operating oil.

As discussed above, the oil film formed between the annular seal land 58 and the end wall of the cylinder block 22 has a higher pressure than that of the oil films between the segment-shaped bearing lands 62 and the end wall of the cylinder block 22. Nevertheless, the contact surfaces between the end wall of the cylinder block 22 and the annular seal land 58 of the valve plate member 38 cannot be subjected to more wear than the contact surfaces between the end wall of the cylinder block 22 and the segment-shaped bearing lands 62. Namely, all of these surfaces can be subjected to uniform wear. This is because each of the radial grooves 60 is defined by a cylindrical surface extended between two adjacent segment-shaped bearing lands, as shown in FIG. 3, so that the cylindrical surface of the radial groove 60 facilitates a penetration of the operating oil from the radial groove 60 into a fine space between the end wall of the cylinder block 22 and the segment-shaped bearing land 62, whereby a uniform wear of the contact surfaces between the end wall of the cylinder block 22 and the annular seal land 58 and segment-shaped bearing lands 62 of the valve plate 38 is ensured during the service life of the pump. In particular, during the rotation of the cylinder block 22, a part of the operating oil passing through each radial groove 60 is entrained by the end wall of the cylinder block 22, and the entrained operating oil can be easily penetrated into the fine space between the end wall of the cylinder block 22 and the segment-shaped bearing land 62 due to the cylindrical surface of the radial groove 60. Preferably, at the boundary between the cylindrical surface of the radial groove 60 and the bearing surface of the segment-shaped bearing land 62, the cylindrical surface of the radial groove 60 forms an angle $\theta$ of about 10 to about 30 degrees to a plane extended from the bearing surface of the segment-shaped bearing land 62.

In this embodiment, a first wedge-like groove 64 is formed in the annular seal land 58 at one edge of the arcuate suction port 38a, which can be defined as a trailing edge with respect to the rotating end wall of the cylinder block 22, whereby the sucking of the operating oil into each cylinder bore 22c through the hole 48 thereof can be gradually stopped. Also, a second wedge-like groove 66 is formed in the annular seal land 58 at one edge of the arcuate discharge port $38b_3$, which can be defined as a trailing edge with respect to the rotating end wall of the cylinder block 22, whereby the discharging of the operating oil from each cylinder bore 22c through the hole 48 thereof can be gradually stopped. Namely, a sudden stoppage of the sucking and discharging of the operating oil is prevented, and thus the pump can be stably operated without vibration.

Figure 4:
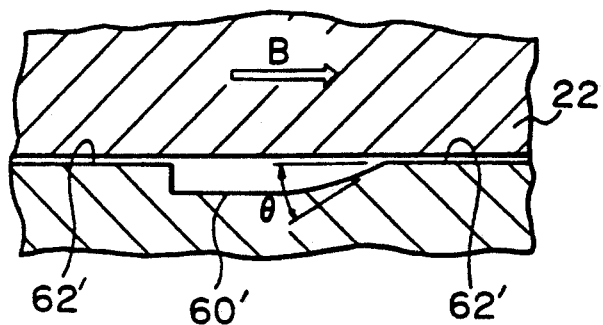
FIG. 4 is a sectional view similar to FIG. 3, showing a modification of the embodiment of FIG. 3.

FIG. 4 shows a modification of the embodiment as shown in FIGS. 1, 2 and 3. In this embodiment, the radial groove 60' is partially defined by a cylindrical surface extended from one side edge of the radial groove 60', which is defined as a trailing side edge with respect to the rotating surface of the end wall of the cylinder block 22, to a bottom of the radial groove 60'. This one-side cylindrical surface of the radial groove 60' also can facilitate the penetration of the operating oil from the radial groove 60' into the fine space between the end wall of the cylinder block 22 and the segment-shaped bearing land 62'. Similarly, at the boundary between the cylindrical surface of the radial groove 60' and the bearing surface of the segment-shaped bearing land 62', the cylindrical surface of the radial groove 60' forms an angle $\theta$ of about 10 to about 30 degrees to a plane extended from the bearing surface of the segment-shaped bearing land 62'.

Figure 5:
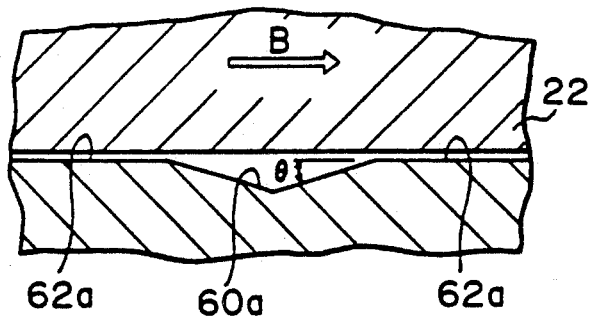
FIG. 5 is a sectional view similar to FIG. 3, showing another embodiment of the present invention.

FIG. 5 shows another embodiment of the present invention, in which a radial groove 60a is defined by a v-shaped cross-sectional surface extended between two side edges thereof. This V-shaped cross-sectional surface of the radial groove 60a also ensures a sufficient penetration of the operating oil from the radial groove 60a into the fine space between the end wall of the cylinder block 22 and the segment-shaped bearing land 62a. Also, preferably, a slope of the V-shaped cross-sectional surface of the radial groove 60a forms an angle $\theta$ of about 10 to about 30 degrees to a plane extended from the bearing surface of the segment-shaped bearing land 62a.

Figure 6:
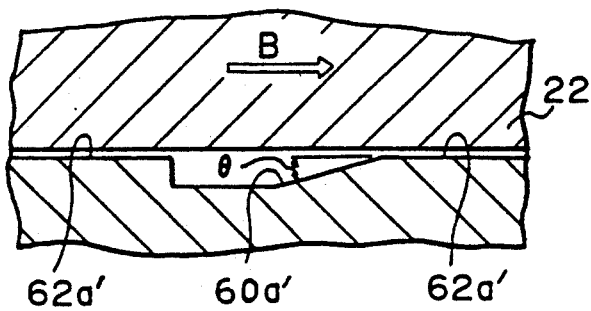
FIG. 6 is a sectional view similar to FIG. 5, showing a modification of the embodiment of FIG. 5.

FIG. 6 shows a modification of the embodiment of FIG. 5. In this modified embodiment, the radial groove 60a' is partially defined by a sloped surface extended from one side edge of the radial oil passage 60a', which is defined as a trailing side edge with respect to a rotating surface of the end wall of the cylinder block 22, to a bottom of the radial oil passage 60a'. This sloped surface of the radial oil passage 60a' also facilitates the penetration of the operating oil into the fine space between the bearing lands 62a' and the end wall of said cylinder block 22 can be also facilitated. Similarly, the sloped surface of the radial groove 60a' forms an angle $\theta$ of about 10 to about 30 degrees to a plane extended from the bearing surface of the segment-shaped bearing land 62a'.

Figure 7A:
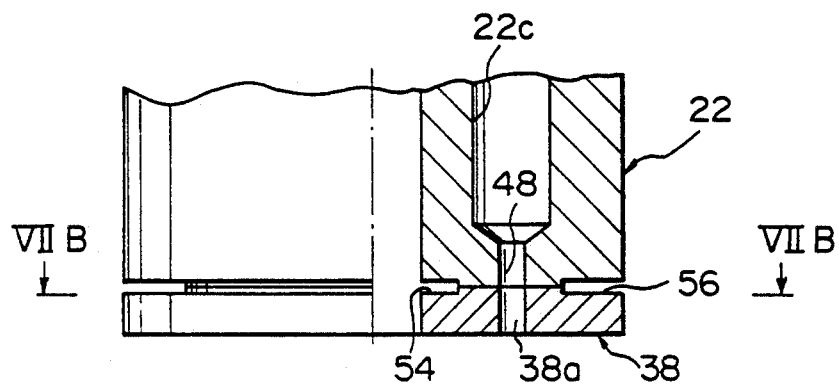
FIG. 7A is a partial sectional view showing a part of a conventional axial piston pump.
Figure 7B:
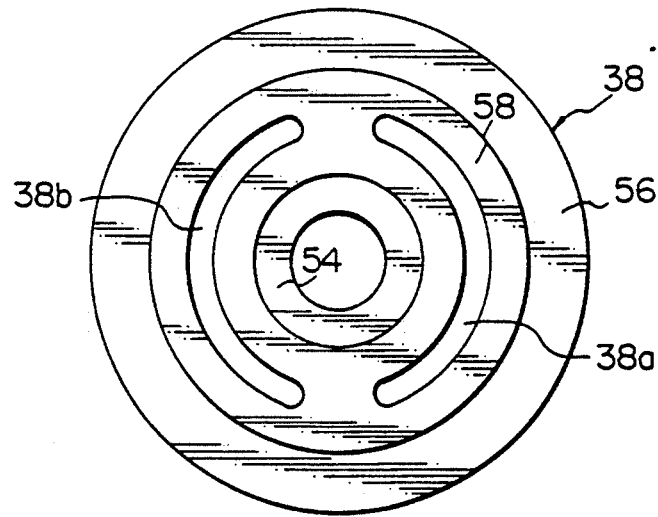
FIG. 7B is a plan view showing a valve plate member of FIG. 7A, as viewed along a line VIIB—VIIB line of FIG. 7A.

FIG. 7 partially shows a conventional axial piston pump of the first-mentioned type. Note, in this drawing, elements similar to those of FIGS. 1, 2 and 3 are indicated by the same reference numerals. As shown in FIGS. 7A and 7B, a valve plate member 38 is provided with inner and outer annular recesses 54 and 56 so that an annular seal land 58 surrounds an arcuate suction port 38a and the arcuate discharge ports 38b. With this arrangement, however, a cylinder block 22 is susceptible to vibrational play during the rotation thereof, because no support of the peripheral annular portion of an end wall of the cylinder block 22 can be provided, as shown in FIG. 7A.

Figure 8A:
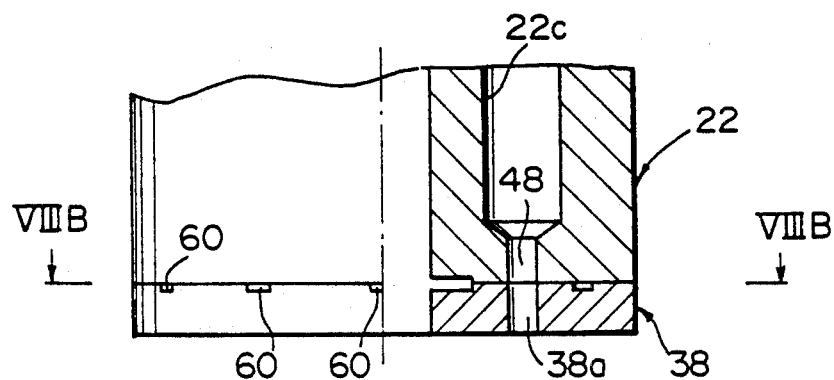
FIG. 8A is a partial sectional view showing a part of another conventional axial piston pump.
Figure 8B:
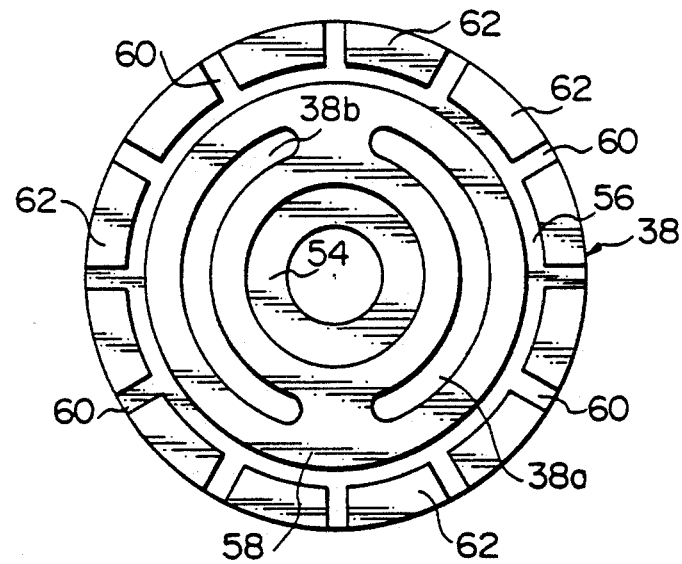
FIG. 8B is a plan view showing a valve plate member of FIG. 8A, as viewed along a line VIIIB—VIIIB line of FIG. 8A.

FIG. 8 partially shows a conventional axial piston pump of the second-mentioned type. Also, in this drawing, elements similar to those of FIGS. 1, 2 and 3 are indicated by the same reference numerals. In this pump, to prevent the vibrational play of the cylinder block 22, a plurality of segment-shaped bearing lands 62 are at regularly spaced intervals along a periphery of a valve plate 38, for supporting a peripheral annular portion of an end wall of the cylinder block, as shown in FIG. 8B. Nevertheless, an annular seal land 58 of the valve plate 38 is still subjected to more wear than the segment-shaped bearing lands 62, for the reasons mentioned hereinbefore. In his case, it is impossible to facilitate a penetration of the operating oil from each radial groove 60 into a fine space between the end wall of the cylinder block 22 and the segment-shaped bearing land 62, because each of the radial grooves 60 has a rectangular cross section, as shown in FIG. 8A.

Finally, it will be understood by those skilled in the art that the foregoing description is of preferred embodiments of the disclosed device, and that various changes and modifications may be made to the present invention without departing from the spirit and scope thereof.

We claim:

1. An axial piston pump for pumping an operating oil through a hydraulic system, said pump comprising:
    a rotary cylinder block having a plurality of cylinder bores formed therein and disposed at regular intervals around a rotational axis thereof, each of said cylinder bores being opened at a bottom thereof through a hole formed in an end wall of said rotary cylinder block;
    a plurality of pistons slidably received in said cylinder bores, respectively;
    a slant cam plate member engaged with said pistons during rotation of said rotary cylinder block, for causing reciprocation of said pistons within the cylinder bores thereof; and
    a fixed valve plate member having a suction port and a discharge port formed therethrough, said end wall of said rotary cylinder block being resiliently pressed against said valve plate member so that said holes of said cylinder bores are operatively connected with said suction and discharge ports of said valve plate member during rotation of said rotary cylinder block, whereby the operating oil is sucked up into each of said cylinder bores in sequence through said suction port of said valve plate member and the corresponding hole of the cylinder bore, and is then discharged from each of said cylinder bores in sequence through said corresponding hole of the cylinder bore and said discharge port of said valve plate member, wherein said valve plate member is provided with an annular seal land formed thereon surrounding said suction and discharge ports with an annular groove around said annular seal land, and a plurality of bearing lands are formed at regularly spaced intervals along a periphery of said valve plate member with a radial groove between every two adjacent bearing lands; said annular groove and said radial grooves being in communication and serving as a guide passage for operating oil leaked from between said annular seal land and said end wall of said rotary cylinder block, and said radial grooves are each at least partially defined by a cylindrical surface extending from a radial side edge of the corresponding radial groove, which side edge is defined as a trailing side edge with respect to a rotating surface of said end wall of said rotary cylinder block, to a bottom of said radial groove, whereby penetration of said operating oil between said bearing lands and said end wall of said rotary cylinder block is facilitated.

2. An axial piston pump as set forth in claim 1, wherein, at the boundary between said cylindrical surface of each radial groove and the bearing surface of the adjacent bearing land, said cylindrical surface forms an angle of about 10 to about 30 degrees to a plane extended from said bearing surface of said bearing land.

3. An axial piston pump as set forth in claim 1, wherein said radial grooves are each defined by a respective cylindrical surface extending from said corresponding radial side edge to an opposite radial side edge.

4. An axial piston pump as set forth in claim 3, wherein, at the boundary between said cylindrical surface of each radial groove and the bearing surface of the adjacent bearing land, said cylindrical surface forms an angle of about 10 to about 30 degrees to a plane extended from said bearing surface of said bearing land.

5. An axial piston pump for pumping an operating oil through a hydraulic system, said pump comprising:
 a rotary cylinder block having a plurality of cylinder bores formed therein and disposed at regular intervals around a rotational axis thereof, each of said cylinder bores being opened at a bottom thereof through a hole formed in an end wall of said rotary cylinder block;
 a plurality of pistons slidably received in said cylinder bores, respectively;
 a slant cam plate member engaged with said pistons during rotation of said rotary cylinder block, for causing reciprocation of said pistons within the cylinder bores thereof; and
 a fixed valve plate member having a suction port and a discharge port formed therethrough, said end wall of said cylinder block being resiliently pressed against said valve plate member so that said holes of said cylinder bores are operatively connected with said suction and discharge ports of said valve plate member during rotation of said cylinder block, whereby the operating oil is sucked up into each of said cylinder bores in sequence through said suction port of said valve plate member and the corresponding hole of the cylinder bore, and is then discharged from each of said cylinder bores in sequence through said corresponding hole of the cylinder bore and said discharge port of said valve plate member, wherein said valve plate member is provided with an annular seal land formed thereon surrounding said suction and discharge ports with an annular groove around said annular seal land, and a plurality of bearing lands are formed at regularly spaced intervals along a periphery of said valve plate member with a radial groove between every two adjacent bearing lands; said annular groove and said radial grooves being in communication and serving as a guide passage for operating oil leaked from between said annular seal land and said end wall of said rotary cylinder block, and said radial grooves are each defined by a V-shaped cross-sectional surface extending between two side edges thereof, whereby penetration of said operating oil between said bearing lands and said end wall of said cylinder block is facilitated.

6. An axial piston pump as set forth in claim 5, wherein, the slope of the V-shaped cross-sectional surface of each radial groove forms an angle of about 10 to about 30 degrees to a plane extended from said bearing surface of said bearing land.

7. An axial piston pump for pumping an operating oil through a hydraulic system, said pump comprising:
 a rotary cylinder block having a plurality of cylinder bores formed therein and disposed at regular intervals around a rotational axis thereof, each of said cylinder bores being opened at a bottom thereof through a hole formed in an end wall of said cylinder block;
 a plurality of pistons slidably received in said cylinder bores, respectively;
 a slant cam plate member engaged with said pistons during rotation of said rotary cylinder block, for causing reciprocation of said pistons within the cylinder bores thereof; and
 a fixed valve plate member having a suction port and a discharge port formed therethrough, said end wall of said cylinder block being resiliently pressed against said valve plate member so that said holes of said cylinder bores are operatively connected with said suction and discharge ports of said valve plate member during rotation of said cylinder block, whereby the operating oil is sucked up into each of said cylinder bores in sequence through said suction port of said valve plate member and the corresponding hole of the cylinder bore, and is then discharged from each of said cylinder bores in sequence through said corresponding hole of the cylinder bore and said discharge port of said valve plate member, wherein said valve plate member is provided with an annular seal land formed thereon surrounding said suction and discharge ports with an annular groove around said annular seal land, and a plurality of bearing lands are formed at regularly spaced intervals along a periphery of said valve plate member with a radial groove between every two adjacent bearing lands; said annular groove and said radial grooves being in communication and serving at a guide passage for operating oil leaked from between said annular seal land and said end wall of said rotary cylinder block, and said radial grooves are each at least partially defined by a sloped surface extending from a radial side edge of the corresponding radial groove, which side edge is defined as a trailing side edge with respect to a rotating surface of said end wall of said cylinder block, to a bottom of said radial groove, whereby penetration of said operating oil between said bearing lands and said end wall of said cylinder block is facilitated.

8. An axial piston pump as set forth in claim 7, wherein, the sloped surface of said radial groove forms an angle of about 10 to about 30 degrees to a plane extended from the bearing surface of said bearing land.

* * * * *

UNITED STATES PATENT AND TRADEMARK OFFICE
CERTIFICATE OF CORRECTION

PATENT NO.   : 5,253,983
DATED        : October 19, 1993
INVENTOR(S)  : S. Suzuki et al It is certified that error appears in the above-indentified patent and that said Letters Patent is hereby corrected as shown below:

Column 3, line 22, before "suction port", "he" should read --the--.

Column 6, line 20, "thethree" should read --the three--.

Column 8, line 29, after "In", "his" should read --this--.

Column 10, line 62, "at" should read --as--.

Signed and Sealed this

Twenty-first Day of June, 1994

Attest:

BRUCE LEHMAN

Attesting Officer   Commissioner of Patents and Trademarks